United States Patent
Hussain et al.

(10) Patent No.: US 11,776,699 B2
(45) Date of Patent: Oct. 3, 2023

(54) SYSTEMS AND METHODS FOR INTEGRATING HEALTHCARE APPLICATIONS

(71) Applicant: Agfa HealthCare NV, Mortsel (BE)

(72) Inventors: Mohannad A. K. Hussain, Waterloo (CA); William Eric Wallace, Kitchener (CA)

(73) Assignee: AGFA HEALTHCARE NV, Mortsel (BE)

( * ) Notice: Subject to any disclaimer, the term of this patent is extended or adjusted under 35 U.S.C. 154(b) by 502 days.

(21) Appl. No.: 16/509,988

(22) Filed: Jul. 12, 2019

(65) Prior Publication Data

US 2021/0012910 A1 Jan. 14, 2021

(51) Int. Cl.
*G16H 80/00* (2018.01)
*H04L 67/141* (2022.01)

(52) U.S. Cl.
CPC ............ *G16H 80/00* (2018.01); *H04L 67/141* (2013.01)

(58) Field of Classification Search
CPC ........ G16H 80/00; G16H 15/00; G16H 40/20; G16H 40/67; G16H 40/63; H04L 67/141; H04L 67/02
See application file for complete search history.

(56) References Cited

U.S. PATENT DOCUMENTS

| | | | | |
|---|---|---|---|---|
| 2003/0058277 A1* | 3/2003 | Bowman-Amuah | | G06F 16/289 715/765 |
| 2003/0069923 A1* | 4/2003 | Peart | | G06F 9/547 709/218 |
| 2007/0061393 A1* | 3/2007 | Moore | | G06Q 10/10 709/201 |
| 2007/0234321 A1* | 10/2007 | Mcdowali | | G06F 9/44526 717/141 |
| 2011/0135075 A1* | 6/2011 | Hubner | | H04M 15/06 379/142.04 |
| 2011/0138059 A1* | 6/2011 | Schleifer | | G06F 9/541 709/227 |

(Continued)

OTHER PUBLICATIONS

HL7 International, "FHIRcast—modern, simple application context synchronization", website last accessed on Jul. 22, 2019 <http://fhircast.org>.

*Primary Examiner* — Jason S Tiedeman
*Assistant Examiner* — Liza Tony Kanaan
(74) *Attorney, Agent, or Firm* — Lewis Rice LLC

(57) ABSTRACT

Systems and methods for integrating a plurality of healthcare software applications. A user initiates one or more software applications required to perform different parts of a healthcare task. The software applications include a local application installed on the user's device and a web-based application accessed through a browser. A host application is launched in order to facilitate local two-way communication between the local application and the web-based application. The host application generates a local communication server on the user device through which the local application and web application communicate. This allows a user to easily and efficiently perform multiple parts of the healthcare tasks. This also allows different healthcare software applications to be integrated without requiring any plug-ins or other integration components to be installed on the user's device.

20 Claims, 3 Drawing Sheets

(56) References Cited

U.S. PATENT DOCUMENTS

| | | | |
|---|---|---|---|
| 2012/0127541 A1* | 5/2012 | Kishida | H04N 1/00228 |
| | | | 358/474 |
| 2012/0239560 A1* | 9/2012 | Pourfallah | G06Q 20/102 |
| | | | 705/40 |
| 2016/0132311 A1 | 5/2016 | Beckman et al. | |
| 2017/0123864 A1 | 5/2017 | Knotts et al. | |
| 2017/0193221 A1 | 7/2017 | Liu et al. | |
| 2018/0262388 A1* | 9/2018 | Johnson | H04L 63/0823 |

* cited by examiner

SYSTEMS AND METHODS FOR INTEGRATING HEALTHCARE APPLICATIONS

FIELD

The embodiments described herein relate generally to systems and methods for providing healthcare software, and in particular systems and methods for integrating different healthcare software applications.

BACKGROUND

The following is not an admission that anything discussed below is part of the prior art or part of the common general knowledge of a person skilled in the art.

Healthcare providers such as clinicians use a number of different software tools in the course of providing healthcare. Different software applications may be used for different aspects of a user's clinical practice, such as accounting software applications, electronic medical record (EMR) applications, medical image viewing applications, clinical reporting applications and so on. A user may interact with multiple software applications in the course of providing care to individual patients, even within a single patient interaction. For instance, a user may interact with separate applications to reviewing medical images, generate clinical reports, and manage billing for a single patient visit.

Using multiple software applications to record and report different aspects of healthcare tasks can be time-consuming and inefficient. In many cases, a user may enter the same information into each application, wasting time and effort that could be better spent treating patients.

The software applications used by clinicians can be provided in different forms. For instance, some software applications may be entirely cloud or web-based while others may be installed locally on a user's device or workstation. To enable integrations between different applications, a user workstation may be provided with pre-installed copies of the different software applications that will be required, along with plug-ins and additional integration components installed on the workstation to allow communication between the different software applications.

However, this approach can be inflexible, as a clinician may be limited to using only those applications installed on a given workstation. This approach also requires the workstation to have significant memory resources, particularly when workstations are used by different clinicians. Ensuring that the clinician workstations are continually upgraded to provide the current applications and application versions required by clinicians on an ongoing basis further involves additional time and expense.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In a broad aspect of this disclosure, systems and methods for integrating a plurality of healthcare software applications may be provided. A user may initiate one or more software applications required to perform different parts of a healthcare task. The software applications can include both a local application installed on the user's device and a web-based application accessed through a browser. A third host application can be launched in order to facilitate local two-way communication between the local application and the web-based application. This may allow a user to easily and efficiently perform multiple parts of the healthcare tasks. This may also allow different healthcare software applications to be integrated without requiring any plug-ins or other integration components to be installed on the user's device or workstation.

The host application may be launched on demand from the web-based or local application. The host application can dynamically configure a local web server to enable and facilitate two-way communication between the web-based application and the local application directly on the user's device.

In accordance with an aspect of an embodiment of the invention, there is provided a healthcare integration system comprising a host application operating locally on a user computer device; and a first healthcare application, wherein the first healthcare application is accessible through a web-browser application operating on the user computer device; where the host application is launchable on-demand to operate a local communication server on the user computing device, and the host application defines a host application domain for the local communication server; and the local communication server enables two-way communication between the first healthcare application and a second healthcare application that operates locally on the user computing device, where the two-way communication occurs directly on the user computing device.

In some embodiments, the first healthcare application includes a host reference that identifies the host application domain of the local communication server, where the host reference is defined in the code of the first healthcare application.

In some embodiments, the host reference further specifies that the host application domain is safe for communication for the first healthcare application.

In some embodiments, the host application is launchable from the first healthcare application.

In some embodiments, the host application is launchable from the second healthcare application.

In some embodiments, the first healthcare application omits the need for any plug-ins or components that are installed locally on the user computing device.

In some embodiments, the first healthcare application omits any plug-ins or components specific to the second healthcare application.

In some embodiments, the host application is built using a Java stack.

In some embodiments, the host application is configured to determine the ports usable for the host application domain of the local communication server dynamically in response to being launched.

In accordance with an embodiment of the invention, there is provided a method of integrating healthcare applications, the method comprising: operating a first healthcare reporting application through a web-browser application operating on a user computing device; operating a second healthcare reporting application that is installed locally on the user computing device; launching a host application to operate on the user computing device; generating, by the host application, a local communication server operating on the user computing device; defining a host application domain for the local communication server; and operating the local communication server to enable two-way communication between the first healthcare reporting application and the second healthcare reporting application directly on the user computing device.

In some embodiments, the first healthcare reporting application includes a host reference that identifies the host application domain of the local communication server, where the host reference is defined in the code of the first healthcare reporting application.

In some embodiments, the host reference further specifies that the host application domain is safe for communication for the first healthcare reporting application.

In some embodiments, the method includes launching the host application in response to a prompt from the first healthcare reporting application.

In some embodiments, the method includes launching the host application in response to a prompt from the second healthcare reporting application.

In some embodiments, the first healthcare reporting application omits any plug-ins or components that are installed locally on the user computing device.

In some embodiments, the first healthcare reporting application omits any plug-ins or components specific to the second healthcare reporting application.

In some embodiments, the host application is built using a Java stack.

In some embodiments, the method includes determining, by the host application, the ports usable for the host application domain of the local communication server in real-time in response to being launched.

It will be appreciated by a person skilled in the art that a system or method disclosed herein may embody any one or more of the features contained herein and that the features may be used in any particular combination or sub-combination.

These and other aspects and features of various embodiments will be described in greater detail below.

DRAWINGS

For a better understanding of the embodiments described herein and to show more clearly how they may be carried into effect, reference will now be made, by way of example only, to the accompanying drawings which show at least one exemplary embodiment, and in which.

Figure 1:
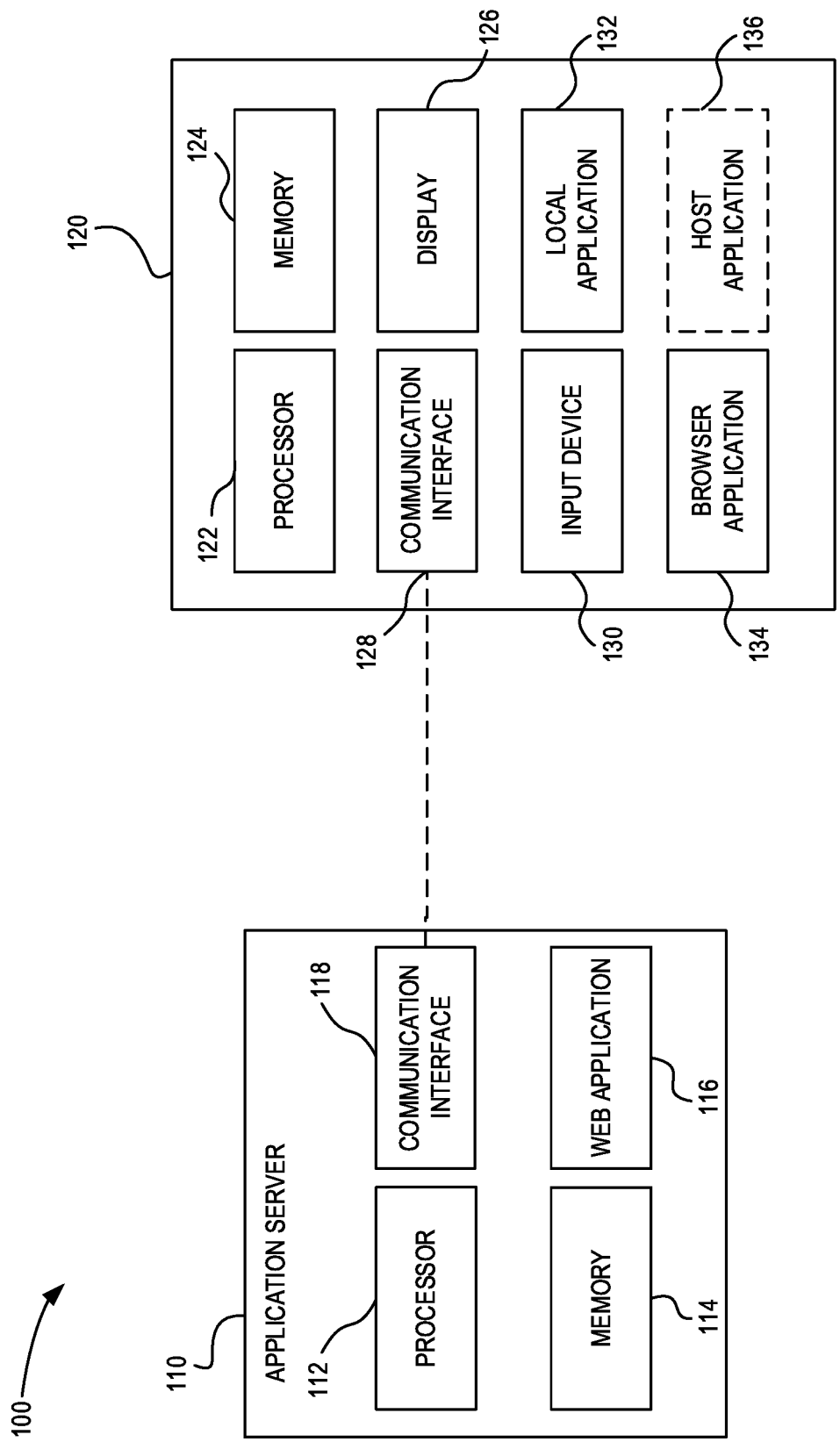
FIG. 1 is a block diagram of a system for providing integrated healthcare applications in accordance with an embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity.

DESCRIPTION OF VARIOUS EMBODIMENTS

Various systems or methods will be described below to provide an example of an embodiment of the claimed subject matter. No embodiment described below limits any claimed subject matter and any claimed subject matter may cover methods or systems that differ from those described below. The claimed subject matter is not limited to systems or methods having all of the features of any one system or method described below or to features common to multiple or all of the apparatuses or methods described below. It is possible that a system or method described below is not an embodiment that is recited in any claimed subject matter. Any subject matter disclosed in a system or method described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling may be used to indicate that an element or device can electrically, optically, or wirelessly send data to another element or device as well as receive data from another element or device. As used herein, two or more components are said to be "coupled", or "connected" where the parts are joined or operate together either directly or indirectly (i.e., through one or more intermediate components), so long as a link occurs. As used herein and in the claims, two or more parts are said to be "directly coupled", or "directly connected", where the parts are joined or operate together without intervening intermediate components.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

Furthermore, any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

The embodiments of the systems and methods described herein may be implemented in hardware or software, or a combination of both. However, preferably, these embodiments are implemented in computer programs executing on programmable computers each comprising at least one module component which comprises at least one processor (e.g. a microprocessor), a data storage system (including volatile and non-volatile memory and/or storage elements), at least one input device, and at least one output device. For example and without limitation, the programmable computers (referred to below as computing devices) may be a personal computer, laptop, personal data assistant, and cellular telephone, smart-phone device, tablet computer, and/or wireless device. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The embodiments described herein provide systems, methods and computer program products for integrating healthcare software application. The term "software application" or "application" refers to computer-executable instructions, particularly computer-executable instructions stored in a non-transitory medium, such as a non-volatile memory, and executed by a computer processor. The computer processor, when executing the instructions, may receive inputs and transmit outputs to any of a variety of input or output devices to which it is coupled. Software applications may include mobile applications or "apps" for use on mobile devices such as smartphones and tablets or other "smart" devices.

A software application can be, for example, a monolithic software application, built in-house by the organization and possibly running on custom hardware; a set of interconnected modular subsystems running on similar or diverse hardware; a software-as-a-service application operated remotely by a third party; third party software running on outsourced infrastructure, etc. In some cases, a software application also may be less formal, or constructed in ad hoc fashion, such as a programmable spreadsheet document that has been modified to perform computations for the organization's needs.

Some software applications may be deployed to and installed on a computing device on which it is to operate. Depending on the nature of the operating system and/or platform of the computing device, an application may be deployed directly to the computing device, and/or the application may be downloaded from an application marketplace. As used herein, software applications that are installed on a computing device prior to use may be referred to as "local" or "native" applications.

Some software applications may be accessed remotely, using other programs that are installed locally on a computing device. For example, some software applications may be accessed through a website or online portal using a browser application that operates locally on a computing device. These "web-based" applications may provide an application environment that operates within the browser application that used to access the corresponding website or portal. In some cases, these web-based applications may require the use of a specific browser application (e.g. Internet Explorer® or Firefox) in order for the web-based application environment to be implemented.

Embodiments described herein can provide systems and methods that allow for integration between a web-based application and a native application on a user's computing device. Embodiments described herein may enable local, two-way communication between the web-based application and the native application without requiring any plug-ins or locally installed components for the web application. The communications between the local application and web application can be facilitated directly on a user's computing device without requiring pre-installation of any software components or plug-ins to provide the two-way communication.

A user may access a first user application in the form of a web-based application through a web-browser application that is installed on the user's computing device. The web-based application may operate entirely within the web-browser application. The web-based application may generate an application environment that is operates contained within the web-browser application used to access the web-based application. In general, the web-based application need not require pre-installation of any plug-ins or components on the user's computing device. Thus, the computing device may omit any plug-ins or components that are installed locally for the web-based application.

A user may also access a second user application in the form of a local or native application that is installed locally on the user's computing device. The local application may provide a local application environment that operates within the operating systems of the user's computing device. The local application may involve one or more associated processes operating on the computing device that are specific to the local application. The local application environment may be provided by the local user application without requiring any intermediary applications, such as a web browser.

The first user application and the second user application may provide functionality associated with various tasks involved in providing healthcare. The first user application and second user application may each be configured to provide functionality that relates to different aspects of the same patient interaction, such as different types of healthcare reporting tasks (e.g. medical accounting vs. clinical report generation). A user, such as a clinician, may interact with both the first user application and the second user application to perform different tasks involved in the same patient interaction, such as using the local user application to review medical images and generate a report and using the web-based application to record patient interaction data required for accounting reports and tracking.

In some cases, the first user application and the second user application may use and/or require the same information to be input. Accordingly, a user may be required to provide the same information to each application. If a user were required to separately enter the same data in each application, additional time would be required to repeat data entry that otherwise might be used for patient care or analysis of acquired medical images. This may also lead to additional errors in transcription or data entry.

In other cases, data generated by one of the user applications may be usable by the other user application. For instance, the results from analysis performed in an image viewing application may be usable in a reporting or recording application. If a user were required to manually transcribe data between the applications, the time required and the risk of data transcription errors would both increase.

Embodiments described herein may facilitate integrations between different applications used by healthcare providers such as clinicians. In embodiments described herein, communication between a first web-based application and a second locally installed application may be enabled directly on the user's computing device. This direct, local communication may be implemented without the use of plug-ins, which may require additional installation time and memory capacity.

A host application can be configured to operate locally on the user computing device. In some cases, the host application may be installed locally on the computing device. For example, the host application may operate continuously as a background application.

In some cases, the host application may be launched by one of the first user application and the second user application. For example, the user application may include an integration launch input or button in the user interface provided to a user of the computing device. The user may then select the launch button to initiate operation of the host application.

The host application can be configured to generate a local communication server on the computing device. The host application can define a host application domain for the local communication server.

The host application can be configured to communicate with the web-based application and the local application. The web application and local application can communicate with the local communication server through the host application domain. The host application may operate as a local relay between the web-based application and the local application.

The host application may provide two-way communication between the web-based application and the local application directly on the user's computing device (i.e. without requiring transmission through a remote web server and in some embodiments without requiring a plug-in for the web-based application). This can allow data on the first user application and second user application to be synchronized locally and in real-time.

The web-based application can be configured to include a host reference corresponding to the host application. The host reference can identify the host application domain on the user's computing device and specify that the host application domain is safe or approved for communication. The host reference can permit the web-based application to communicate locally with the host application through the local communication server.

In some cases, the host reference may be defined in the code of the web-based application. The code of the web-based application may include a code segment identifying the host reference for the web application. For example, the web-based application may include a reference to the host application in JavaScript.

In some cases, the web-based application may determine the host reference dynamically. For example, the web-based application may determine the host reference using the Internet Protocol (IP) address of the computing device that initiated operation of the web-based application through the browser application. The web-based application can then use the IP address of the requesting computing device to define the host reference for a session of communication between the web-based application and the host application. Depending on the network used by the computing device, the IP address may be an external network address or the IP address may be internal to an organizational network.

Referring now to FIG. 1, shown therein is a block diagram of a system 100 for providing integrated healthcare applications. System 100 includes an application server 110 and a user workstation in the form of computing device 120. The workstation 120 and server 110 can be coupled over a network, such as the Internet. In some cases, the computing device 120 and server 110 may be connected over an internal organizational network, such as a network configured within a hospital or other healthcare clinic.

The network may be constructed from one or more computer network technologies, such as IEEE 802.3 (Ethernet), IEEE 802.11 and similar technologies. Typically, the connections between computing device 120, server 110 and the Internet may be made via a firewall server (not shown).

Computers and computing devices such as device 120 and server 110 may be connected to the network or a portion thereof via suitable network interfaces. In some cases, the workstation 120 and server 110 may be located remotely from one another and the workstation 120 may connect to server 110 via the Internet and/or using networks such as a telecommunications network.

The computing device 120 may be a computer such as a smart phone, desktop or laptop computer, which can connect to a network via a wired Ethernet connection or a wireless connection. The computing device 120 has a processor 122, a memory 124 that may include volatile memory and non-volatile storage, at least one communication interface 128, input devices 130 such as a keyboard and trackpad, output devices such as a display device 126 and speakers, and various other input/output devices as will be appreciated.

Processor 122 is a computer processor, such as a general purpose microprocessor. In some other cases, processor 122 may be a field programmable gate array, application specific integrated circuit, microcontroller, or other suitable computer processor.

Processor 122 is coupled to display device 126, which is a suitable display for outputting information and data as needed by various computer programs. In particular, display device 126 may display graphical user interfaces (GUI) that include application environments with which a clinician may interact. The clinician device 120 may execute an operating system, such as Apple iOS™, Microsoft Windows™, GNU/Linux, or other suitable operating system.

Communication interface 128 is one or more data network interface, such as an IEEE 802.3 or IEEE 802.11 interface, for communication over a network.

Processor 122 is coupled, via a computer data bus, to memory 124. Memory 124 may include both volatile and non-volatile memory. Non-volatile memory stores computer programs consisting of computer-executable instructions, which may be loaded into volatile memory for execution by processor 122 as needed. It will be understood by those of skill in the art that references herein to workstation 120 as carrying out a function or acting in a particular way imply that processor 122 is executing instructions (e.g., a software program/application) stored in memory 124 and possibly transmitting or receiving inputs and outputs via one or more interface. Memory 124 may also store data input to, or output from, processor 122 in the course of executing the computer-executable instructions.

Computing device 120 may have a number of applications installed locally thereon. Although shown as separate elements, it will be understood that local application 132, browser application 134 and host application 136 may be stored in memory 124.

The server 110 may be a computer such as a desktop or server computer, which can connect to a network via a wired connection (e.g. an Ethernet connection) or a wireless connection. The server 110 has a processor 112, a memory 114 that may include volatile memory and non-volatile storage, at least one communication interface 118, and a web application 116. The processor 112, memory 114, and communication interface 118 may be implemented in generally the same manner as with processor 122, memory 124, and communication interface 128 respectively.

Although shown as separate elements, it will be understood that web application 116 may be stored in memory 114. Optionally, server 110 may include additional input or output devices, although this is not required. As with all devices shown in system 100, there may be multiple servers 110, although not all are shown. In some cases, server 110 may be distributed over a plurality of computing devices, for instance operating as a cloud server providing the web application 116 as a software as a service (SaaS) application. As with clinician device 120, references to acts or functions by server 110 imply that processor 112 is executing computer-executable instructions (e.g. a software program) stored in memory 114.

Memory 114 may also store a database. In some example embodiments, the database may be a relational database. In other embodiments, the database may be a non-relational database, such as a key-value database, NoSQL database, a graph database, or the like. The database can be used to store data usable by the computing device 120, including medical imaging data such as breast images and associated breast image data and characteristics. The medical imaging data may be stored as a plurality of medical imaging records, which may include medical imaging records for one or more patients. The medical imaging data may be stored in various formats, such as using a DICOM (Digital Imaging and Communications in Medicine) image format. The medical imaging data may be generated by radiological and other imaging procedures (e.g. ultrasound images, CT scans, MRIs X-rays etc.), and may also include markers and/or standardized codes such as codified markers defined using national/international standards (e.g. HL7, DICOM).

As noted above, a browser application 134 may be stored on the workstation 120. Although shown separately from memory 124, it will be understood that browser application 134 may be stored in memory 124. In general, browser application 134 may be implemented using any software application that enables a user to access websites over a network such as the Internet. The browser application 134 may also be used to access sites and applications that are internal to an organizational network such as sites provided on an intranet. In general, the browser application 134 can be configured to enable a user of computing device 120 to access and launch web application 116 through an internal network such as an organizational intranet or an external network such as the Internet.

For example, browser application 134 may be implemented using browser applications such as Internet Explorer®, Mozilla Firefox, Google Chrome®. In some cases, a particular browser application (e.g. Internet Explorer®) may be required to access a given web application 116. Although only one browser application 134 is shown, it will be understood that two or more browser applications 134 may be installed and operable on the computing device 120. When browser application 134 is launched, an instance of a browser application process may be instantiated on computing device 120. The number of instances of browser application processes that are instantiated for a given browsing session may vary depending on the browser application (e.g. some browser application may instantiate separate processes for each browser tab, while other browser application may instantiate only a single browser process even for multiple browser tabs).

A local user application 132 may also be stored on the workstation 120. Although shown separately from memory 124, it will be understood that local application 132 may be stored in memory 124. The local user application 132 generally refers to an application that is pre-installed in memory 124 and can operate locally on the workstation 120. A user may launch the local user application 132 without an intermediary application, such as a browser. Launching local user application 132 may also involve instantiating an instance of a local application process on the computing device 120. The local user application 132 may then provide the user with an interaction environment configured to provide functionality related to an aspect of a healthcare task being performed.

The local user application 132 may be configured to provide various functions associated with healthcare operations and tasks. For example, the local user application 132 may be configured to provide functionality associated with healthcare reporting, image viewing, artificial intelligence processing and so forth. In some cases, there may be a plurality of local user applications 132 installed on device 120. Each of the local user applications may be configured with different functionality to enable a user to perform various different tasks by selecting the appropriate local user application. This may also allow different users to perform tasks associated with their particular area of practice, which may allow clinicians having different specialties to share workstation 120.

As one example, the local user application 132 may be an image viewing application. An image viewing application may provide a user of the workstation 120 with user interfaces for managing and reviewing medical image data stored in memory 124 and retrieved from a remote imaging server and/or archive database. The image viewing application may communicate with a remote imaging server (e.g. an imaging database stored in memory 114 on server 110) to request and receive medical image data from the server. A user may interact with an image viewing application to review medical images acquired from a patient or patients. In some cases, the user may annotate the medical images or define notes or other data associated with the reviewed medical images.

As another example, the local user application 132 may be a healthcare reporting application. For instance, the local user application 132 may be a PowerScribe application. A user may interact with the PowerScribe application on the computing device 120 to perform radiology reporting tasks. The reporting application may be configured to enable a user to input data collected from a patient, and/or review data (e.g. studies) associated with a patient, in order to generate a report regarding the patient interaction or prognosis for example.

The data generated by the local user application 132 may be stored using defined communication protocols. For instance, medical imaging data used by an image viewing application may be stored as a plurality of medical imaging records, which may include medical imaging records for one or more patients. The medical imaging data may be stored in various formats, such as using a DICOM (Digital Imaging and Communications in Medicine) image format. The medical imaging data may be generated by radiological and other imaging procedures (e.g. ultrasound images, CT scans, MRIs X-rays etc.), and may also include markers and/or standardized codes such as codified markers defined using national/international standards (e.g. HL7, DICOM).

As noted above, web application 116 may be provided by an application server 110. The web application 116 may be provided as a cloud application accessible to the workstation 120 over an internal organizational network or through an external network such as the Internet. Various different types of software applications used in healthcare may be provided as cloud applications or Software-as-a-Service (SaaS).

A user can interact with browser application 134 operating on computing device 120 to navigate to a website or portal associated with the web application 116. The user may then select or launch the web application 116 within the browser application 134. The web application 116 can then provide an interactive user environment to the user through browser application 134. The web application 116 may depend on the browser application 134 to enable the interactive user environment of web application 116 to be provided. The web application 116 can operate as a transient application on computing device 120. The web application 116 may not require any application instructions to be stored in non-volatile memory of memory 124. This may allow a clinician user of computing device 120 to initiate operation of web application 116 without requiring administrator privileges and/or pre-installed of web application 116 or associated components.

The web application 116 can be configured to provide functionality associated with a healthcare tasks or tasks that is different from the functionality provided by local application 132. For example, the web application 116 may be an accounting application such as Xero. A user may interact with the accounting application to track tasks performed in respect of a patient and facilitate billing.

In some cases, it may be desirable for the local application 132 and the web-based application 116 to share and/or synchronize date. For example, an application such as an accounting application may use data from a clinical reporting application to determine the tasks that need to be billed. In other cases, a reporting application may share data with an image viewing application to perform functions such as identifying and tracking pathologies and/or monitoring treatment plans.

In some cases, real-time synchronization between the web application and the local application may be provided. Real-time synchronization may be useful to ensure that measurements on images are identified correctly. Real-time data synchronization may also be important to ensure that the user is reviewing the correct study and/or report. For example, where one of the applications is a report application and the other application is an image viewing application, and a user changes the study being reviewed in the image application a notification may be provided to indicate that that the report and images are no longer synchronized. In some cases, real-time synchronization may also ensure that the local application and web application perform certain functions in tandem to avoid loss of synchronization (e.g. updates, close report, report complete, next image operations).

In order to ensure that the local application 132 and web-based application 116 can share and/or synchronize data, the system 100 can include a host application 136. The host application 136 can operate on the computing device 120 to facilitate communication between the local application 132 and web-based application 116. The host application 136 may enable communication between the local application 132 and web-based application 116 without requiring the communications to be routed through a remote web server. The host application 136 may also enable communication between the local application 132 and web-based application 116 without requiring a plug-in for the web-based application 116.

In some embodiments, the computing device 120 may include a plug-in related to the web-based application, that is nonetheless unrelated to communication between the web-based application 116 and the local application 132 (and also unrelated to the host application 136). For example, java applets may be used to allow the web-based application 136 to operate by supporting operation of web-based application 136 (as well as other java applications). In general, however, the embodiments described herein enable an instance of a host application 136 to be initiated from the web-based application 116 without a plug-in or other locally installed component being used or called by the web-based application 116. The embodiments described herein also enable two-way communication between the web-based application 116 and local application 132 without any plug-ins or other installed components of the web-based application 116 specific to the local application 132.

The host application 136 can be configured to generate a local communication server. The local communication server can be generated to operate locally on the computing device 120. The local communication server can enable two-way communication between the local application 132 and web-based application 116 directly on the computing device 120.

The web-based application 116 can be configured to communicate with the local communication server. Similarly, the local application 132 can be configured to communicate with the local communication server. Communications between the web-based application 116 and the local application 132 can be routed through the local communication server. This may allow two-way communication between web application 116 and local application 132 without requiring data transmissions to remote servers, e.g. without requiring data transmissions to server 110.

Running host application 136 on computing device 120 may involve launching a separate process on the computing device 120. This can ensure that the host application 136 is locally addressable on computing device 120. The locally running host process may provide a local server address that can be communicated directly using http calls to the address defined by the process (e.g. http://localhost:port).

As shown, the host application 136 may be installed on computing device 120. Thus, the host application 136 can be instantiated directly on computing device 120. For instance, the host application 136 may operate as a background application on computing device 120. When operating as a background application, the host application 136 may determine that a session of web-based application 116 has been initiated that may require communication/synchronization with a local application 132. The host application 136 may then generate a local server to enable communication between the web-based application 116 and the local application 132. The web-based application 116 and local application 132 may transmit and receive data via the local server that allows for data and/or actions to be synchronized between the web-based application 116 and local application 132.

In some embodiments, host application 136 may not be pre-installed on computing device 120. For example, host application 136 may be launched by the web-based application 116. Additionally or alternatively, the host application 136 may be launched by the local application 132.

One or both of the web-based application 116 and the local application 132 may include a selectable user interface icon that allows a user to manually initiate operation of the host application 136. The host application 136 may be launched on-demand in response to a user selecting the launch button in the user interface of either the web-based application 116 or the local application 132.

In some embodiments, the web-based application 116 may be configured to automatically launch the host application 136. For instance, web-based application 116 may determine that synchronization with local application 132 is desired based on user interactions within the web-based application 116. The web-based application 116 may then launch the host application 136 to facilitate synchronization. Additionally or alternatively, the local application 132 may be configured to automatically launch the host application 136. This may allow the local communication server to be instantiated on-demand as needed to provide communication or synchronization between local application 132 and web application 116.

The local communication server need not be installed or persistent on local computing device 120 prior to being instantiated. For example, host application 136 may operate the local communication server as a transient application on computing device 120. This may facilitate activation of the local communication server by a clinician user that may not have elevated privileges on computing devices 120 (e.g. administrator access that may otherwise be required to install a new application on device 120). Operating the local communication server as a transient application may also allow the application to be instantiated on computing device 120 rapidly. This may facilitate initiating a synchronization process as well as re-loading the local communication server in case of a crash.

In some cases, the web-based application 116 may be configured to cause the local application 132 to be launched. For example, a user may select a synchronization icon within the environment of the web-based application 116. The web-based application 116 may then communicate with, or launch, host application 136 to determine whether the local application 132 is operating on the computing device 120. If an instance of the local application 132 is currently operational, the host application 136 may then provide communication between the web-based application 116 and local application 132. If an instance of the local application 132 is not currently operational, the host application 136 may initiate an instance of local application 132. The host application 136 may then facilitate communications and synchronization once local application 132 is running.

The host application 136 can define a host application domain for the local communication server. The local application 132 and web application 116 can be configured to identify the address space of the host application domain as suitable for communication.

The web application 116 can include a host reference identifying the host application domain of the local communication server. In some cases, the host reference may be defined in the code of the web application 116. In other cases, the host reference may be defined dynamically. For instance, the web application 116 may include a script that, when run, can be used to define the host reference identifying the host application domain. This host reference script can specify that the host application domain is safe for the web application 116 to interact with.

For example, the host reference script in web application 116 may rely on device address data from computing device (such as the internal or external IP address and/or hostname of the end user's workstation 120) when identifying the host application domain of the local communication server. The device address data may be used or provided by computing device 120 when accessing web application 116 through browser application 134.

In some cases, the host application 136 may determine the ports usable for the host application domain of the local communication server once the host application 136. The usable ports may be determined dynamically by the host application 136 in response to being launched. In other cases, a specified port or ports may be reserved for the local communication server e.g. where the host application 136 operates as a background application on computing device 120.

The host application 136 may also be configured to facilitate communications between applications regardless of the operating system that is implemented on computing device 120. The host application 136 can be configured to use platform neutral or platform independent communication protocols to allow two-way communication between the web application 116 and a local application 132 that is installed on computing device 120, in various different operating systems. This may facilitate operation of the host application 135 without requiring specific plug-ins or extensions to be installed on computing device 120.

For example, the host application 136 configure the local communication server to communicate using the Hypertext Transfer Protocol (HTTP). Since most if not all implementations of browser applications 134 are configured to support HTTP communication, this may ensure that web application 116 can communicate with the local communication server regardless of the specific browser that is operating on computing device 120. This may also support communications with older computing device, and facilitate integrations without requiring updates to the hardware or operating system of computing device 120.

The local communication server may also be configured to communicate with the local application 132 using HTTP. This may ensure that host application 136 can be effectively implemented on computing device 120, for instance where host application 136 is launched in response to a trigger from web application 116.

In some embodiments, the host application 136 may be configured using a Java stack. This may facilitate operation of host application 136 on various different operating systems for computing device 120 (e.g. Windows, Macintosh, Linux etc.) without requiring specific plug-ins or extensions to be installed on computing device 120. This may also facilitate operation of host application 136 on legacy systems that may use older operating systems.

In other cases, the host application 136 may be configured using different software frameworks or programming languages, such as the .NET framework. In some such cases, the host application 136 may be specifically defined for an operating system that is running on computing device 120.

The application server 110 and clinician device 120 may have various additional components not shown in FIG. 1. For example, additional input or output devices (e.g., keyboard, pointing device, etc.) may be included beyond those shown in FIG. 1.

It should be understood that the system 100 may be implemented in hardware or software or a combination of both. Specifically, various modules of medical system 100 are preferably implemented in computer programs executing on programmable computers, each comprising at least one processor, a data storage system, at least one input device and at least one output device. Without limitation, the programmable computers may be a mainframe computer, server, personal computer, laptop, personal data assistant, cellular telephone, smartphone or tablet device.

Figure 2:
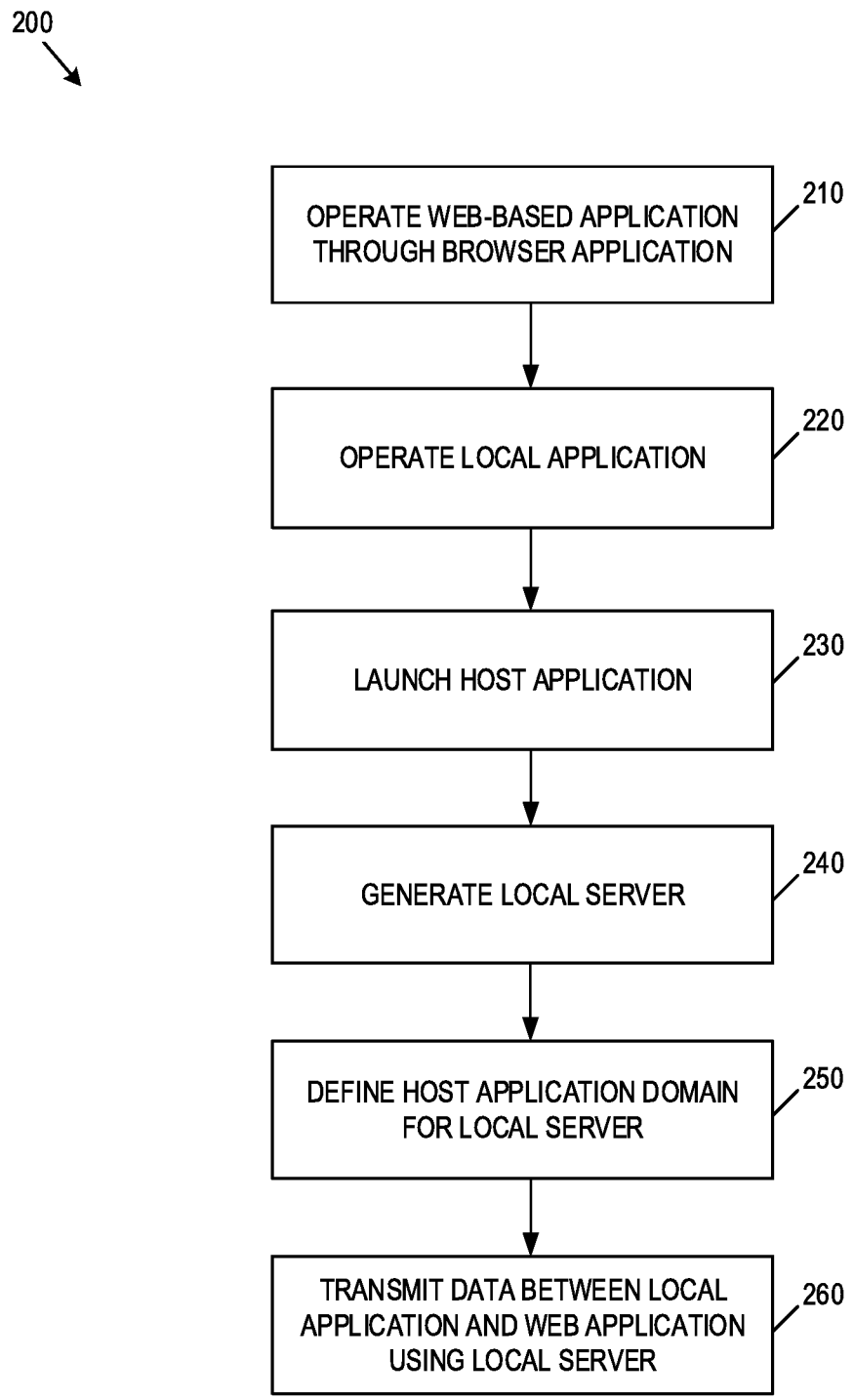
FIG. 2 is a flowchart diagram illustrating the steps of a method for integrating healthcare applications within the system of FIG. 1.

Referring now to FIG. 2, shown therein is a flowchart illustrating an example method 200 for providing integration between healthcare software applications. Method 200 is an example of a method that may be performed by a healthcare integration system such as system 100.

At 210, a first healthcare application can be operated on the computing device 120. The first healthcare application may be a web-based application that operates through a web-browser application that is operating on the user device 120. A user of computing device 120 may interact with the web-browser application to access the first healthcare application. The first healthcare application may then provide a web-based user environment within the browser application.

The first healthcare application may provide functionality associated with one or more tasks to be performed in relation to providing healthcare. For instance, the first healthcare application may provide a clinician with functionality related to recording or tracking patient interactions, such as reviewing patient records and/or conducting billing for patient interactions and other tasks.

The first healthcare application may operate within the browser application without requiring any plug-ins or locally installed components. In some cases, the computing device 120 may not include any plug-ins, locally installed components, extensions, and so forth specific to the first healthcare application.

At 220, a second healthcare application can be operated on the computing device 120. The second healthcare application may be a local or native application that is installed on the user device 120. A user of computing device 120 may instantiate the second healthcare application by selecting an icon or other link within the operating system environment of the computing device 120.

The second healthcare application may also provide functionality associated with one or more tasks to be performed in relation to providing healthcare. For instance, the second healthcare application may provide a clinician with functionality related to reviewing medical images or tracking patient interactions, such as reviewing patient records and/or generating clinical reports and other tasks. Typically, the functionality provided by the second healthcare application will differ from the functionality provided by the healthcare application. That is, the second healthcare application may provide functionality related to a different aspect of a healthcare interaction or task At 230, a host application can be launched on the user computing device 120. In some cases, a user may launch the host application through the first healthcare application or second healthcare application by selecting an interface item within the environment of the healthcare application. In other cases, the host application may be launched automatically by the first healthcare application or second healthcare application when the respective healthcare application determines that synchronization between the first and second healthcare application is desirable or required.

For example, the host application may be defined using Java. The first healthcare application may include a java network launch protocol corresponding to the host application (netboot.jnlp). The launch protocol may be associated with a launch icon selectable by a user, or with trigger conditions defined in the first healthcare application specifying when the host application is to be launched. The JNLP protocol can then be used to launch the host application on the computing device 120 from the first software application operating in the browser application on computing device 120. The host application may then operate as a local or native application running on computing device 120.

In some cases, the host application may operate continuously as a background application on computing device 120. The host application may then be activated in response to a trigger (manual or automatic) from the first healthcare application or second healthcare application.

The host application can operate locally on the computing device 120. A host application process may be instantiated on computing device 120 when the host application is launched.

In some cases, a user of the computing device 120 may launch the second healthcare application through interaction with the first healthcare application. For example, a user may select a synchronization function corresponding to the second healthcare application within the environment of the first healthcare application. The first healthcare application may then communicate with the host application (and in some cases also launch the host application) to initiate the second healthcare application locally on the computing device 120.

In response to a request from the first healthcare application, the host application may determine whether the second healthcare application is currently operating on the computing device 120. If the second healthcare application is not yet active, the host application may launch the second healthcare application on computing device 120.

At 240, the host application can generate a local communication server. The local communication server can be configured to operate locally on the computing device 120. The local communication server can provide an intermediary with which both the first and second healthcare applications can communicate in order to provide two-way communication between the first and second healthcare applications locally on the computing device 120. This may provide direct communication between a local application and web-based application without requiring plug-ins or extensions or transmissions to remote application servers.

At 250, a host application domain can be defined for the local communication server. The host application domain can be defined by the host application when the local communication server is initially configured.

In some cases, when generating the local communication server, the host application may determine the ports usable by the local communication server. The usable ports may be determined dynamically, and in real-time, in response to the host application being activated to generate the local communication server.

In some cases, the usable ports may be pre-defined or reserved for the local communication server. For instance, where the host application operates continuously as a background application on the computing device 120 the ports usable by the local communication server may be reserved.

The first healthcare application can be configured to communicate with the host application domain of the local communication server. For example, the first healthcare application may include a host reference that is defined in code that identifies the host application domain. The host reference may further specify that the first healthcare application is permitted to communication with the host application domain. For instance, the host reference may be defined in JavaScript in the first healthcare application.

In some cases, the host reference in the first healthcare application may identify the host application domain dynamically. For example, the host reference may include a script usable to identify the host application domain that is generated for the local communication server. The web application may use the IP address (internal or external) of the computing device 120 that accessed the web application through the browser in order to determine the host application domain. For example, the web application may use Cross-Origin Resource Sharing (CORS) to dynamically identify the host application domain.

At 260, the local communication server can operate to enable two-way communication between the first healthcare application and the second healthcare application. The local communication server may allow the first healthcare application and the second healthcare application to transmit and receive data from on another directly on the computing device 120. This may facilitate real-time updates and synchronization between the first healthcare application and the second healthcare application.

The local communication server may be configured to transmit data to each of the first healthcare application and the second healthcare application using platform-independent communication protocols. For example, the local communication server may use the Hypertext Transfer Protocol (HTTP) to transmit data to and from each of the first healthcare application and the second healthcare application. This may allow the web application and local application to synchronize while operating on various different browser applications and operating systems.

Figure 3A:
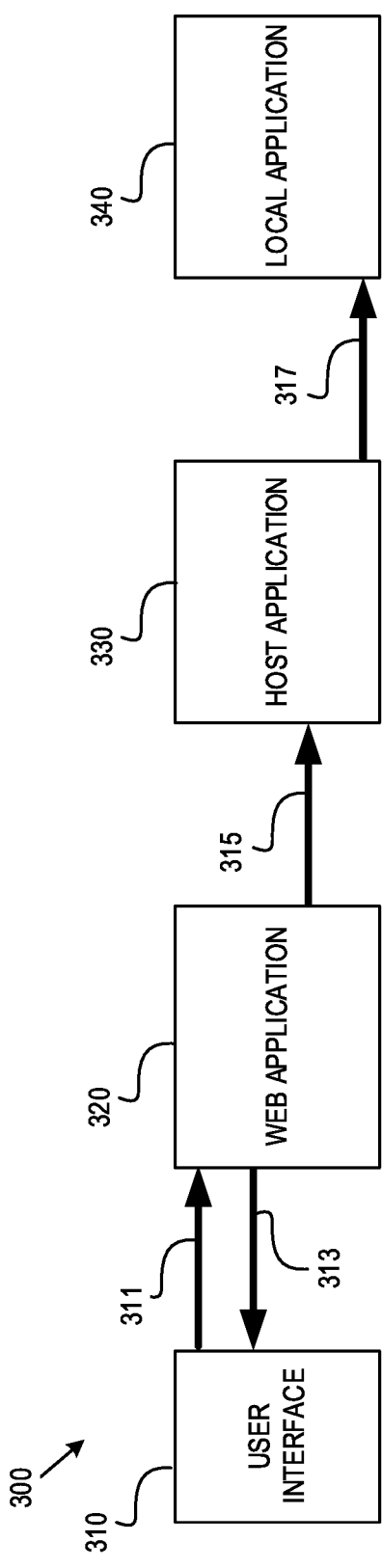
FIG. 3A is a diagram illustrating an application initiation data flow in an example system for providing integrated healthcare applications in accordance with an embodiment.

Referring now to FIG. 3A, shown therein is an example system 300 illustrating data flow between a user interface 310, a web application 320, a host application 330 and a local application 340. The system 300 illustrates an example of data flow that occurs when application integration between a web-based application 320 and a local application 340 is launched from the web-based application 320.

The web application 320, host application 330 and local application 340 may generally correspond to the web application 116, the host application 136 and the local application 132. The user interface 310 may be provided in various forms by the computing device 120 and may include the display 126, input device 130 and various other types of input and/or output devices.

As shown in system 300, an integration request 311 may be sent from user interface 310 to web application 320. The integration request 311 may be sent in response to a user selecting an integration icon within the environment of the web application 320 that is displayed in a browser application 134 operating on the computing device 120. The integration request 311 may specify to the web application 320 that integration with a specified local application 340 should be initiated.

The web application 320 may then transmit a host launch message 313 to user interface 310 (i.e. to computing device 120). In some cases, the host launch message 313 may instruct the computing device 120 to activate a host application 330 that is already installed on computing device 120.

In other cases, however, the host launch message may include host application data that can be downloaded to the computing device 120. The computing device 120 may use the host application data to instantiate an instance of the host application 330. For example, the host launch message may include a java network launch protocol usable to instantiate the host application 330 as a temporary application on computing device 120. The host application 330 may then generate a local communication server that operates on computing device 120.

The web application 320 can also transmit a host reference message 315 to the host application 330. The host reference message 315 may specify that the host application 330 is included as a "safe" Javascript provider for the host application 330.

Figure 3B:
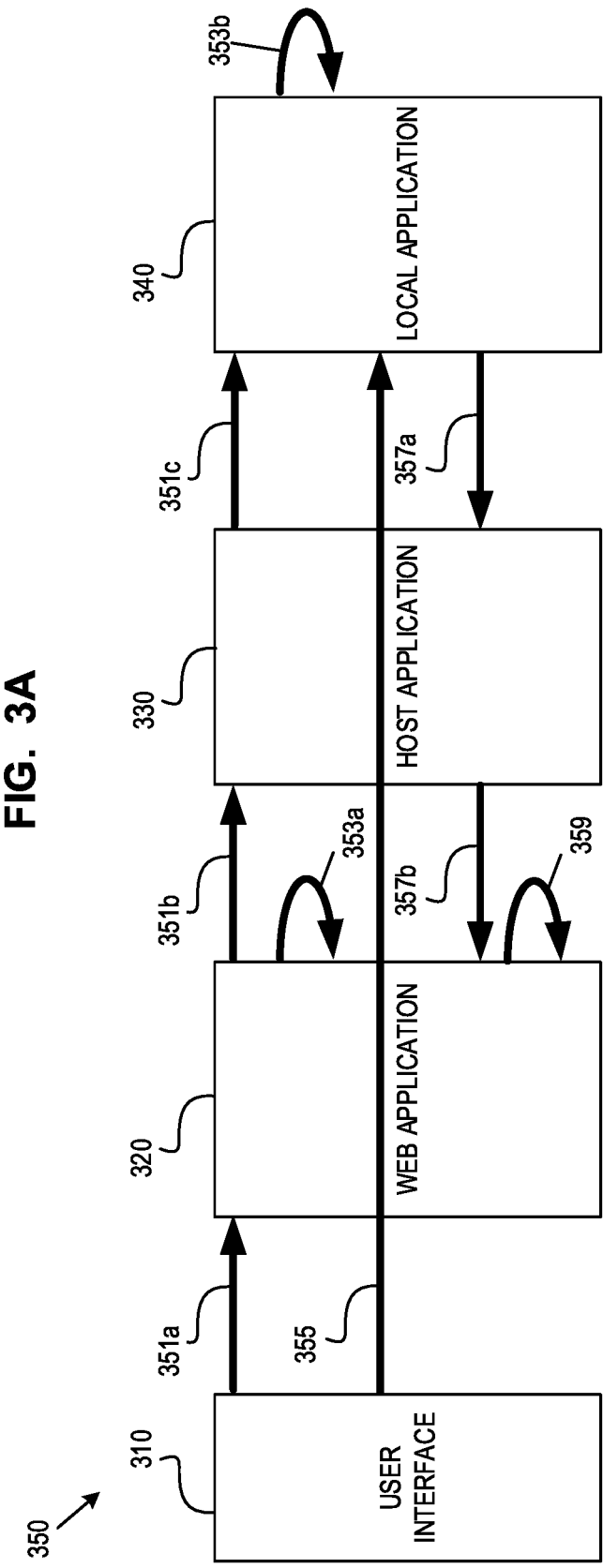
FIG. 3B is a diagram illustrating an operational data flow in an example system for providing integrated healthcare applications in accordance with an embodiment.

The host application 330 can also determine whether the local application 340 is operational on the computing device 120. If the local application 340 is not currently operational (i.e. there is no instance of local application 340 currently running on the computing device 120), the host application 330 may transmit a launch and authenticate message 317 to the local application 340. The launch and authenticate message 317 may configure computing device 120 to launch an instance of local application 340, and to authenticate the local application 340 with the local communication server. The local communication server may then provide communication between local application 340 and web application 320, an example of which is shown in FIG. 3B and described herein below.

Table 1, below, provides an example of pseudo-code that may be used to provide the data transmissions shown in FIG. 3A.

TABLE 1

EXAMPLE CODE FOR SYSTEM 300

```
End User->+Web App: Invoke Integration
Web App->-End User: Download and start\nTemp application
  (e.g. JNLP)
Web App->Temp App: Include as "safe" Javascript provider
Temp App->Native App: Launch and authenticate
```

Referring now to FIG. 3B, shown therein is another example system 350 illustrating data flow between a user interface 310, a web application 320, a host application 330 and a local application 340.

The system 350 illustrates an example of data flow that occurs when application integration between a web-based application 320 and a local application 340 is occurring on an on-going basis. System 350 illustrates an example of application integration between a web-based application 320 used to review medical images and a local application 340 used to generate clinical reports. The data flow shown in system 350 may occur repeatedly while a user is interacting with web application 320 and local application 340. For example, the data flow shown in system 350 may occur once for each synchronization action, such as once for each patient study that is being reported.

A study request message 351a can be transmitted from the user interface 310 to the web application 320. For instance, a user may select a study for which the user will generate a report. The study request message 351a can include identifying data associated with the requested study, such as patient identifier data, image type, image date and so forth. The user may select an icon corresponding to that study within the interface of the web application 320.

The web application 320 can then transmit a relayed study request message 351b to the local communication server generated by host application 330. The relayed study request message 351b can also include the identifying data associated with the requested study. The host application 330 can then transmit a further relayed study request message 351c to the local application 340. The study request message 351c also includes study identifying data associated with the requested study.

In response to receiving the study request message 351a, the web application 320 can access study data at 353a that corresponds to the requested study. The web application 320 can open or access the study data within the environment of the web application 320 for review by a user.

Similarly, the local application 340 can also access study data at 353b that corresponds to the requested study in response to receiving the relayed study request message 351c. The local application 340 can open or access the study data within the environment of the local application 340 for review by a user. The study data accessed, used, or displayed by local application 340 and web application 320 may differ.

For instance, the web application 320 may present medical images associated with a study while the local application 340 may present patient data and related medical history. The web application 320 and local application 340 may also provide different interactive functionality. For instance, web application 320 may allow a user to review, navigate and annotate medical images associated with the requested study. The local application 340 may provide an interactive reporting template that the user can complete in order to generate a clinical report.

In some cases, the user's interactions with web application 320 (e.g. annotations or markings in the medical images) may be synchronized with the local application 340 (or vice versa). For instance, where a user identifies margins within a medical image in the web application 320, the system 350 may be configured to automatically synchronize the evaluated size of the margin with a corresponding field in the interactive template within local application 340 via the local communication server provided by host application 330. As will be appreciated, various other types of data synchronization may be performed between the web application 320 and local application 340.

The user may interact with both the web application 320 and local application 340 in order to review medical images and prepare a report. When the user has completed the report, the user may input a finalization message 355 to the local application 340. The finalization message 355 can indicate to local application 340 that the report is complete. In response to the finalization message, the local application 340 may store and/or transmit the completed report.

The local application 340 can also transmit a report complete message 357a to the local communication server generated by host application 330. The report complete message 357a may include identifying data corresponding to the study selected at 351 and to the report that was completed by the local application 340. The communication server can then transmit a relayed completed message 357b to the web application 320.

At 359, the web application 320 may refresh the data associated with the study. In some cases, at 359, the web application 320 may access a subsequent study. For instance, the user at 351a may indicate a series of studies to be reviewed. In such cases, the web application 320 may then access data associated with the subsequent study and transmit a relayed request message 351b related to the subsequent study. The process shown in FIG. 3B may then be repeated. In other cases, a user may input a separate study request message to select a new or different study to be reviewed and reported.

In response to completion of the report, the local application 340 and web application 320 may release the data associated with the study. This may allow the study data to be accessed by other clinicians, e.g. where the computing device 120 is used in a networked environment.

Table 2, below, provides an example of pseudo-code that may be used to provide the data transmissions shown in FIG. 3B.

TABLE 2

EXAMPLE CODE FOR SYSTEM 350

```
loop Repeat per action (study to be reported)
    parallel {
        End User->Web App: Launch study for reporting
        Web App->Temp App: Relay request from End User
        Temp App->Native App: Relay request from End User
    }
    parallel {
        Web App->Web App: Open study for viewing images
        Native App->Native App: Open study for reporting
    }
    End User->Native App: Author report and finalize
    parallel {
        Native App->Temp App: Notify of action
        Temp App->Web App: Notify of action
    }
    Web App->Web App: Reaction (e.g. refresh or next study)
end
```

As used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A healthcare integration device comprising:
a processor; and
a non-volatile memory coupled to the processor, the non-volatile memory storing instructions executable by the processor to provide one or more applications;
wherein the processor is configured by the instructions to:
operate a host application locally on the healthcare integration device;
operate a first healthcare application through a web-browser application operating on the healthcare integration device; and
operate a second healthcare application locally on the healthcare integration device and outside the web-browser application environment;
wherein
the host application is launchable on-demand from both the first healthcare application and from the second healthcare application, the host application being launchable in response to determining, by the first healthcare application or the second healthcare application, that communication is to be provided between the first healthcare application and the second healthcare application,
the host application is configured to generate, after being launched, a local communication server on the healthcare integration device, wherein the local communication server is uninstantiated prior to being generated by the host application thereby enabling the local communication server to be automatically instantiated on-demand in response to determining, by the first healthcare application or the second healthcare application, that communication is to be provided between the first healthcare application and the second healthcare application;
the host application operates outside the web-browser application environment;
the host application defines a host application domain for the local communication server; and
the local communication server enables two-way communication between the first healthcare application and the second healthcare application, wherein the two-way communication occurs directly on the healthcare integration device.

2. The device of claim 1, wherein the first healthcare application includes a host reference that identifies the host application domain of the local communication server, wherein the host reference is defined in the code of the first healthcare application.

3. The device of claim 2, wherein the host reference further specifies that the host application domain is safe for communication for the first healthcare application.

4. The device of claim 1, wherein the host application is launchable from the first healthcare application in response to a user selecting a launch button in a user interface of the first healthcare application; or in response to automatically determining, by the first healthcare application, that synchronization with the second healthcare application is desired based on user interactions within the first healthcare application.

5. The device of claim 1, wherein the host application is launchable from the second healthcare application in response to a user selecting a launch button in a user interface of the second healthcare application; or in response to automatically determining, by the second healthcare application, that synchronization with the first healthcare application is desired.

6. The device of claim 1, wherein the first healthcare application omits the need for any plug-ins or components that are installed locally on the healthcare integration device.

7. The device of claim 1, wherein the first healthcare application omits any plug-ins or components specific to the second healthcare application.

8. The device of claim 1, wherein the host application is configured to determine the ports usable for the host application domain of the local communication server dynamically in response to being launched.

9. A method of integrating healthcare applications on a user computing device, the user computing device comprising a processor and a non-volatile memory, and the method comprising:
operating, by the processor, a first healthcare reporting application through a web-browser application operating on the user computing device;
operating, by the processor, a second healthcare reporting application that is installed locally on the non-volatile memory of the user computing device and operates outside the web-browser application environment;
launching, by the processor, a host application, from one of the first healthcare application and the second healthcare application, in response to determining that communication is to be provided between the first healthcare application and the second healthcare application, wherein the host application operates on the user computing device and the host application operates outside the web-browser application environment;
generating, by the host application after the host application is launched, a local communication server operating on the user computing device, wherein the local communication server is uninstantiated prior to being generated by the host application thereby enabling the local communication server to be automatically instantiated on-demand in response to determining, by the first healthcare application or the second healthcare application, that communication is to be provided between the first healthcare application and the second healthcare application;
defining, by the processor, a host application domain for the local communication server; and
operating, by the processor, the local communication server to enable two-way communication between the first healthcare reporting application and the second healthcare reporting application directly on the user computing device.

10. The method of claim 9, wherein the first healthcare reporting application includes a host reference that identifies the host application domain of the local communication server, wherein the host reference is defined in the code of the first healthcare reporting application.

11. The method of claim 10, wherein the host reference further specifies that the host application domain is safe for communication for the first healthcare reporting application.

12. The method of claim 9, further comprising launching the host application in response to a prompt from the first healthcare reporting application, the prompt generated in response to a user selecting a launch button in a user interface of the first healthcare application; or in response to automatically determining, by the first healthcare application, that synchronization with the second healthcare application is desired based on user interactions within the first healthcare application.

13. The method of claim 9, further comprising launching the host application in response to a prompt from the second healthcare reporting application, the prompt generated in response to a user selecting a launch button in a user interface of the second healthcare application; or in response to automatically determining, by the second healthcare application, that synchronization with the first healthcare application is desired.

14. The method of claim 9, wherein the first healthcare reporting application omits any plug-ins or components that are installed locally on the non-volatile memory of the user computing device.

15. The method of claim 9, wherein the first healthcare reporting application omits any plug-ins or components specific to the second healthcare reporting application.

16. The method of claim 9, further comprising determining, by the host application, the ports usable for the host application domain of the local communication server in real-time in response to being launched.

17. The system of claim 1, wherein the host application is configured to determine whether the second healthcare application is instantiated on the healthcare integration device and in response to determining that the second healthcare application is not instantiated, provide a launch message to the second healthcare application, the launch message defined to cause the second healthcare application to be launched.

18. The system of claim 1, wherein the local communication server is operated as a transient application on the healthcare integration device.

19. The method of claim 9, further comprising: determining, by the host application, whether the second healthcare application is instantiated on the healthcare integration device; and providing, by the host application, a launch message to the second healthcare application in response to determining that the second healthcare application is not instantiated, the launch message defined to cause the second healthcare application to be launched.

20. The method of claim 9, wherein the host application operates the local communication server as a transient application on the healthcare integration device.

* * * * *